(12) United States Patent
 Littlefair

(10) Patent No.: US 11,717,236 B2
(45) Date of Patent: Aug. 8, 2023

(54) INTRAORAL COORDINATE SYSTEM OF DENTITION FOR THE DESIGN AND PLACEMENT OF DENTAL IMPLANTS

(71) Applicant: Jessi Lew Pty Ltd, Homebush (AU)

(72) Inventor: Darren Littlefair, Homebush (AU)

(73) Assignee: Jessi Lew Pty Ltd, Homebush (AU)

( * ) Notice: Subject to any disclaimer, the term of this patent is extended or adjusted under 35 U.S.C. 154(b) by 0 days.

(21) Appl. No.: 17/597,615

(22) PCT Filed: Jul. 31, 2020

(86) PCT No.: PCT/IB2020/057284
§ 371 (c)(1),
(2) Date: Jan. 13, 2022

(87) PCT Pub. No.: WO2021/019516
PCT Pub. Date: Feb. 4, 2021

(65) Prior Publication Data
US 2022/0202377 A1    Jun. 30, 2022

Related U.S. Application Data

(60) Provisional application No. 62/880,962, filed on Jul. 31, 2019.

(51) Int. Cl.
*A61B 6/00* (2006.01)
*A61B 6/03* (2006.01)
(Continued)

(52) U.S. Cl.
CPC ............. *A61B 6/032* (2013.01); *A61B 6/12* (2013.01); *A61B 6/145* (2013.01); *A61B 6/4085* (2013.01);
(Continued)

(58) Field of Classification Search
CPC .......... G01N 2223/076; G01N 23/2204; G01N 23/223
See application file for complete search history.

(56) References Cited

U.S. PATENT DOCUMENTS

| 10,206,757 B2 | 2/2019 | Pettersson |
| 2005/0163342 A1 | 7/2005 | Persky |

(Continued)

FOREIGN PATENT DOCUMENTS

| EP | 3 517 040 A1 | 7/2019 |
| WO | 2018/152742 | 2/2017 |

(Continued)

OTHER PUBLICATIONS

International Search Report dated Sep. 28, 2020 in PCT/IB2020/057284.

(Continued)

*Primary Examiner* — Dani Fox
(74) *Attorney, Agent, or Firm* — Andrew Berks; Gallet Dreyer & Berkey LLP

(57) ABSTRACT

This invention provides a mapped dental Cone Beam Computer Tomography (CBCT) workspace for the planning of placement of dental implants in the oral cavity. The workspace includes a template coordinate system in the oral cavity of a patient by placing a radiographic template having at least three radiographic markers of predetermined shape, size, and positions in the oral cavity, wherein the predetermined position is relative to at least one anatomical feature (natural or artificial) in the oral cavity. With this method, only a single CBCT scan is required. The CBCT scan is used to create a CBCT workspace with a coordinate system based on the radiographic template. Within the workspace, Implant Planning Software can be used to plan dental implants.

10 Claims, 9 Drawing Sheets

(51) Int. Cl.
  *A61B 90/00* (2016.01)
  *G16H 30/40* (2018.01)
  *A61B 6/12* (2006.01)
  *A61B 6/14* (2006.01)
  *A61C 7/00* (2006.01)
  *A61C 9/00* (2006.01)
  *A61C 13/00* (2006.01)
  *A61B 34/10* (2016.01)
  *A61C 1/08* (2006.01)

(52) U.S. Cl.
  CPC ............ *A61B 6/425* (2013.01); *A61B 6/4233* (2013.01); *A61B 6/5211* (2013.01); *A61B 6/587* (2013.01); *A61B 90/39* (2016.02); *A61C 7/002* (2013.01); *A61C 9/0046* (2013.01); *A61C 9/0053* (2013.01); *A61C 13/0004* (2013.01); *G16H 30/40* (2018.01); *A61B 6/501* (2013.01); *A61B 2034/105* (2016.02); *A61B 2090/3966* (2016.02); *A61C 1/084* (2013.01)

(56) References Cited

U.S. PATENT DOCUMENTS

| 2011/0123080 | A1 | 5/2011 | Sebok |
| 2013/0131505 | A1 | 5/2013 | Daon et al. |
| 2018/0279975 | A1 | 10/2018 | Doron et al. |
| 2019/0046307 | A1 | 2/2019 | Schulter et al. |
| 2019/0142548 | A1 | 5/2019 | Scheffer |

FOREIGN PATENT DOCUMENTS

| WO | 2017218040 A1 | | 12/2017 |
| WO | WO2018/152742 | * | 8/2018 |

OTHER PUBLICATIONS

International Preliminary Report on Patentability dated Nov. 19, 2021 in PCT/IB2020/057284.

* cited by examiner

INTRAORAL COORDINATE SYSTEM OF DENTITION FOR THE DESIGN AND PLACEMENT OF DENTAL IMPLANTS

CROSS REFERENCE TO RELATED PATENT APPLICATION

This application claims priority to U.S. Patent Application 62/880,962, filed Jul. 31, 2019, the entire contents of which are incorporated by reference.

FIELD OF THE INVENTION

This invention pertains to the establishment of an intraoral coordinate system from CBCT scanning data of the dentition for the design, construction, and implantation of prosthetic teeth using radiographic templates having radiographic markers with predetermined coordinates.

BACKGROUND

Dental Cone Beam Computer Tomography (CBCT or CT) is technology used to generate three-dimensional images of dental structures such as teeth, soft tissue, bone and nerve paths of the craniofacial region of a patient (CT Data).

CT Data is used to diagnose and plan for a variety of procedures by dentists or dental specialists such as oral surgeons and periodontists. One common procedure making use of CT Data is the replacement of missing teeth using dental implants as anchor points for a prosthetic restoration. The CT Data is used to assist with the planning of the location of the dental implants.

One or more dental implants can be embedded into a patient's maxilla or mandible and a variety of dental prostheses can be affixed to the implant(s). Typical prosthetic treatments include:
- an implant abutment secured to the implant and dental crown connected to the abutment;
- an implant support bridge replacing several teeth and secured to multiple dental implants using screws; or
- a removable implant supported overdenture that "clips" to attachments that are attached to the dental implants.

The CT Data is imported into software (Implant Planning Software) used by the dentist or dental specialist such as an oral surgeon and periodontist. The software allows the user to view the CT Data in various cross sectional and three-dimensional views. These views are used to determine suitable sites for the implants, including ensuring there is adequate bone density for the implant body to be embedded and avoiding vital structures such as the sinuses and the inferior alveolar nerve.

Part of the implant placement planning utilizes knowledge of the tooth positions in the planned final prosthesis ("Final Tooth Position"). This helps to ensure the implants are positioned such that there is adequate space beneath the tooth and above the implant for the support structure of the prosthesis. Knowing the Final Tooth Position can also help plan the angulation/axis of the implants to ensure the screw access emerges from a desirable face of the replacement tooth.

The problem addressed by this invention is superimposing the patient's anatomical data (CT Data), with the prosthetic data (Final Tooth Position). The solution requires importing the Final Tooth Position into the Implant Planning Software and transforming the Final Tooth Position data set so that it is positioned and orientated correctly within the CT Data.

A method known as the "Dual Scan" method has been used to align the Final Tooth Position with the CT Data. This method involves taking a patient's existing denture or the fabrication of a duplicate of their denture (an "appliance"), wherein the material of the appliance is radiolucent, meaning that it is transparent to x-rays. Within the appliance, three or more geometric features (Radiographic Markers) made from a material that is opaque to x-rays (Radiopaque) are installed. The appliance with the Radiographic Markers is termed a Radiographic Template. The Radiographic Template is worn by the patient and a CBCT scan is taken. The CT scan is termed CT Data 1 (102). An exemplary CT scan is shown in FIG. 1.

Following that, the Radiographic Template is scanned placed in a CT scanner and scanned ex vivo. The data from this scan is termed CT Data 2 (104). Because the patient is not exposed to any radiation during this scan, a higher resolution scan may also be taken. This is shown in FIG. 2A.

A difficulty of this method is that the radiographic markers, despite being radiopaque, can be difficult to locate at this stage, and are unclear in FIG. 2A. For clarity, four markers (110) that were actually present in the scan of FIG. 2A are highlighted in FIG. 2B.

Both sets of data (CT Data 1 and CT Data 2) are then imported into Implant Planning Software, and tools within the software are used to extract the segments of CT Data that contain the Radiographic Markers (Marker Segmentation). The Marker Segmentation of CT Data 2 (104) is aligned to the Marker Segmentation of CT Data 1 (102) using tools within the Implant Planning Software. The entire dataset of CT Data 2 is moved during the alignment process; thus, we now have the denture as represented by the CT Data correctly superimposed within the anatomical CBCT scan of the patient (FIG. 3)

Although this is common practice, there are several disadvantages to this method including:
- The placement of markers is not defined in advance, so the second scan of the Radiographic Template is necessary to establish a coordinate system for the template.
- Even with a higher resolution CBCT scan of the radiographic template, there are still significant inaccuracies in the positions of the markers, so there is a low confidence in the accuracy of the alignment process.
- The prior art Dual Scan method is an incremental process. No common reference, no landmark or datum is established, so as the mouth is modified during the surgery the coordinate system shifts, which is a problem. Any changes to the Final Tooth Position will require a new appliance being fabricated and a new CBCT scan taken.
- Other prosthetic information cannot be readily superimposed, such as three-dimensional geometric data representing the patient's soft tissue (Gingiva) that is not necessarily visible within the CT Data.

The instant inventors have developed improvements to the above technique that alleviates and eradicates many of the disadvantages.

SUMMARY OF THE INVENTION

The invention relates to aspects of dental implant planning. The restorative dentist or oral surgeon needs to determine the placement of the implant given the patient CT data. Patient dental structures such as teeth, soft tissue, bone and nerve paths of the craniofacial region of a patient and the planned final position of prosthetic teeth. Therefore, precise visualization of the patient's oral cavity is required.

Accordingly, this invention provides a mapped CBCT workspace for the planning of placement of dental implants in the oral cavity. The workspace includes a radiographic CBCT workspace radiographic template coordinate system in the oral cavity of a patient by placing a radiographic template having at least three radiographic markers of predetermined shape, size, and positions in the oral cavity, wherein the predetermined position is relative to at least one anatomical feature (natural or artificial) in the oral cavity; taking a single CBCT scan of the oral cavity of the patient with the radiographic markers in the predetermined position; and establishing a radiographic CBCT coordinate system by identifying the radiographic markers with the CT scan data and determining the position of the markers; establishing a radiographic template coordinate system (prosthetic CAD (Computer Aided Design) workspace from FIG. 11) from the predetermined location and geometry of the radiographic markers on the radiographic template, and importing the radiographic template coordinate system into Implant Planning Software; and mapping the radiographic template coordinate system to the radiographic CBCT coordinate system or vice-versa with a mathematical transformation.

In an embodiment the mapped CBCT workspace has radiographic markers selected from spheres or another 3D geometric shape, whereby each geometric shape is a discreet radiographic marker.

In an embodiment the mapped CBCT workspace includes radiographic markers selected from spheres or another 3D geometric shape, whereby the geometric data of the radiographic markers are combined to form a workspace.

In an embodiment the template is a prosthetic appliance placed in the mouth of the patient with three or more radiographic markers at known positions.

In an embodiment the template is a jig with three or more radiographic markers at known positions, wherein the jig is placed in the mouth of the patient in a location that can be fixed with respect to the anatomy of the mouth.

In an embodiment, a method is provided of establishing a final tooth position of a dental prosthetic design overlaid with the CBCT scan using the mapped CBCT workspace.

In an embodiment, a method of establishing a mapped CBCT workspace is provided by best-fit alignment of marker segmentation of the CBCT scan and the 3D geometry of the radiographic markers. In an embodiment, a best fit alignment is provided between the geometric center of the pre-determined markers and the geometric center of the markers determined within the CBCT scan.

In an embodiment, a method is provided for planning dental implant locations and trajectories in the intraoral cavity of patient in need of dental implants, comprising establishing a final tooth position of a dental prosthetic design overlaid with a CBCT scan using the mapped CBCT workspace, and selecting appropriate screw locations and trajectories within Implant Planning Software, wherein the screw trajectories intersect with the final tooth positions in a dentally acceptable location.

DETAILED DESCRIPTION

The current invention has the advantages of avoiding a second CBCT scan, that is required by the prior art "dual scan" method, and it provides superior precision in the mapping of natural and prosthetic oral structures, so it results in more precise visualizations of the mouth for planning positions of dental prostheses.

In the prior art "dual scan" method described above, the radiographic markers may be of an arbitrary geometry, and placed arbitrarily within an appliance that is worn by the patient during the CBCT scan. The radiographic markers (also known as Fiducial Markers) may be placed by hand on the appliance.

While this allows the dentist to correlate the radiographic template with the CT Data, it does not allow the dentist to subsequently correlate any other prosthetic data because the position of the markers is not predetermined. For this reason, a second CT scan of the template must be performed to establish a coordinate system for the markers. Thus, the prior art method requires two CT scans. Moreover, the precision of the data from the second CT scan is imprecise and can complicate the design process because of this impression.

CAD Designed Radiographic Template

Figure 1:
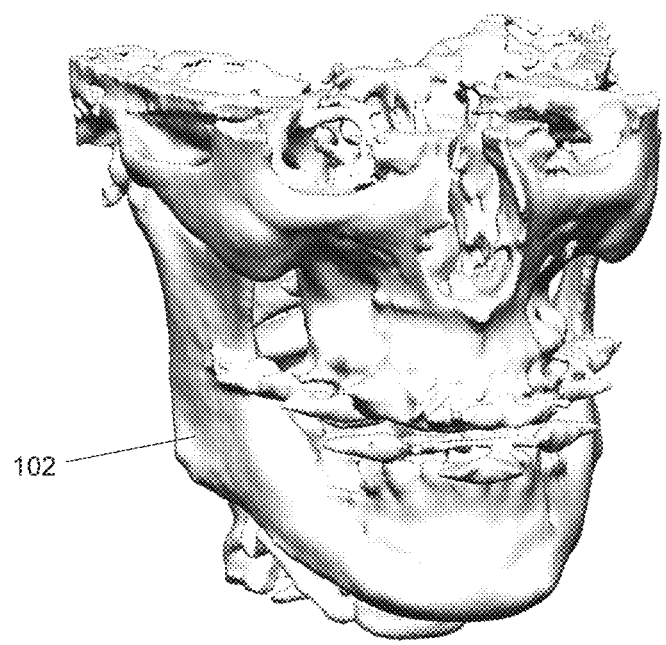
FIG. 1 A CBCT scan of a patient, wearing a radiographic template.
Figure 2A:
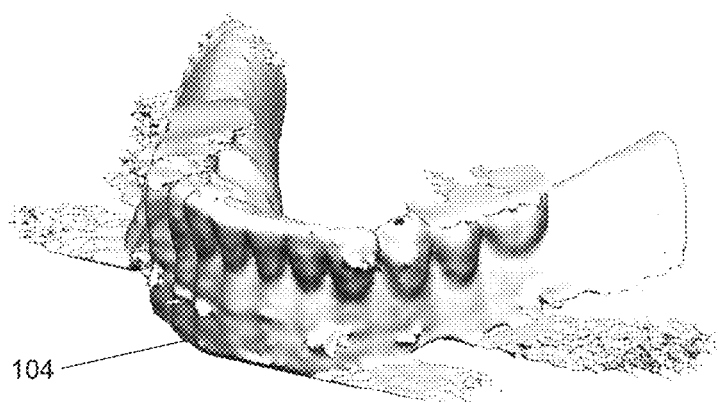
FIG. 2A. A CBCT scan of a radiographic template.
Figure 2B:
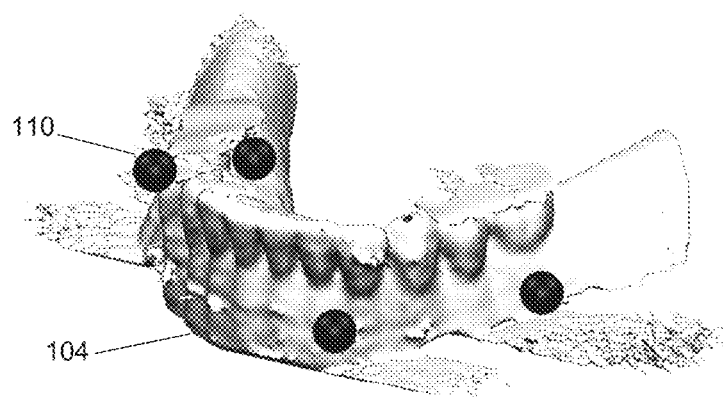
FIG. 2B. A CBCT scan of a radiographic template with the radiographic markers (4) highlighted.
Figure 3:
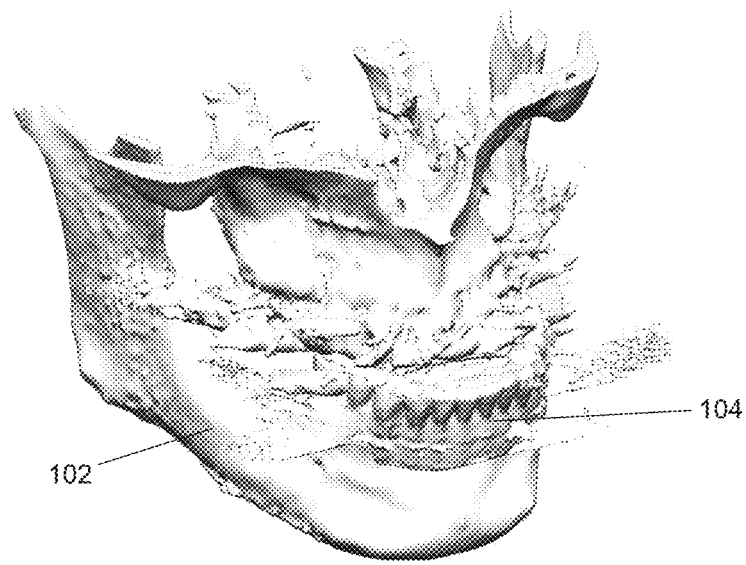
FIG. 3. Aligned CBCT data of the patient scan and the template scan.
Figure 4:
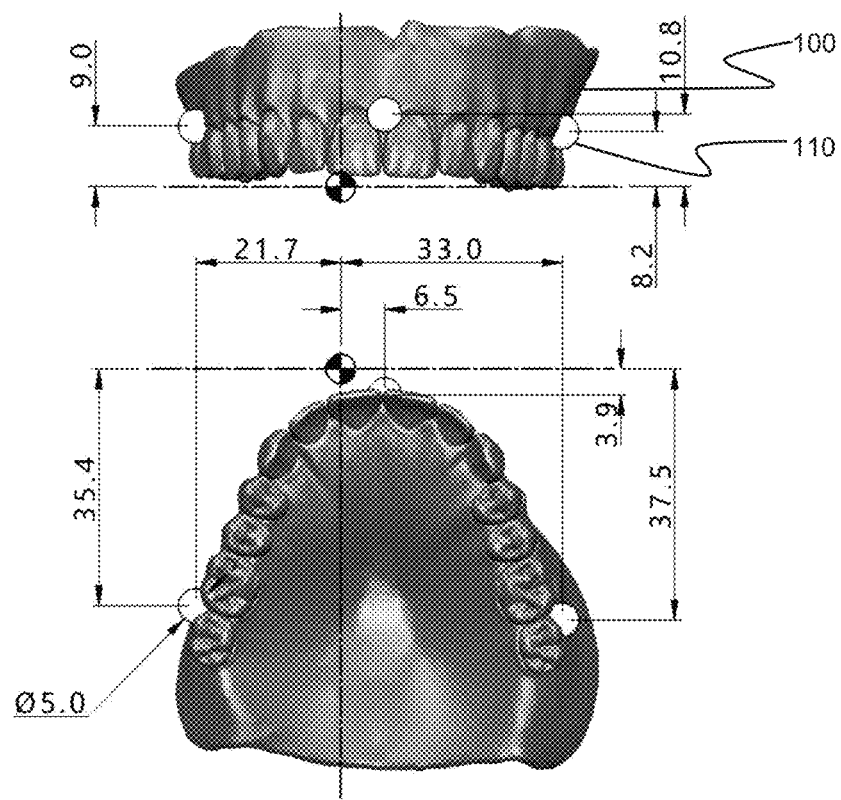
FIG. 4. A CAD designed radiographic template. Radiographic markers (white spheres) are at predetermined coordinates.

This invention addresses these problems by providing a radiographic template 100 that has radiographic markers 110 that are of a predictable and predetermined size and arbitrary position within the template, such as shown in FIG. 4. The shape, size, and position of each radiographic marker (geometric data) is determined in advance of the acquisition of the CBCT scan, as illustrated by the exemplary dimensions shown in FIG. 4. The position of each marker is thus defined within a 3D coordinate system.

The radiographic markers 110 may be spheres or some other 3D geometric shape whereby each geometric shape is a discrete radiographic marker. The markers are illustrated as spheres in the drawings. However, the radiographic markers can be other shapes such as tetrahedrons, cubes, or icosahedrons.

Figure 4A:
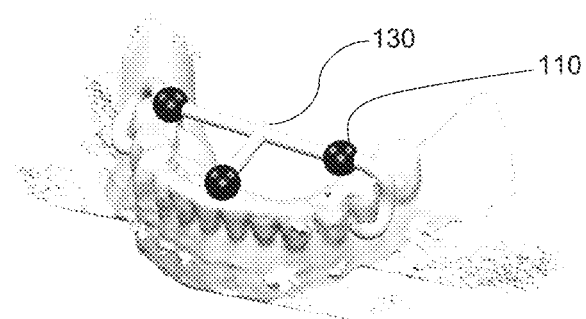
FIG. 4A. Jig with radiopaque markers overlaid into the lower dentition.

The template can be a dental appliance as shown in FIG. 4 that fits over the gums and any existent teeth, or it may be a jig (130), i.e., a simple framework with radiographic markers that can be laid into the mouth curing the CBCT scan procedure (FIG. 4A). For example, a jig 130 might comprise three or more arms radiating from a central support with a radiographic marker 110 on the end of each arm. As with the other radiographic templates of this invention, the positions of each radiographic marker in a 3D coordinate system must be determined prior to insertion into a patient's mouth and the acquisition of a CBCT scan. The jig embodiment requires a more substantial number of existent teeth that can support the jig in a fixed location. In another embodiment, screws can be placed in the patient's mouth that support a jig embodiment and provide fixed positions or "landmarks" that link the radiographic markers to a patient's anatomy.

The Radiographic Template 100 may be designed to be worn by the patient while the CBCT scan is taken. The input to the design of the Radiographic Template is the geometry of the patient's jaws on which the appliance will sit.

Using Computer Aided Design (CAD) software, geometry data that has been recorded and stored digitally can be manipulated, edited or used to construct additional geometry also recorded and stored digitally.

Typically, an impression of a patient's existing teeth or gingiva is taken to obtain Model Data. This can be done either by taking a physical impression that is a negative or imprint of the patient's jaw using an appropriate material. A cast of the jaw is then produced from this impression. The cast is then scanned using a 3D scanning device that can record the geometry of the cast and store that data in a digital format. Alternatively, a virtual impression can be captured using an intra-oral scanner that captures the jaw geometry and records this data in a digital format directly. The Model Data is then imported into CAD design software.

Figure 5:
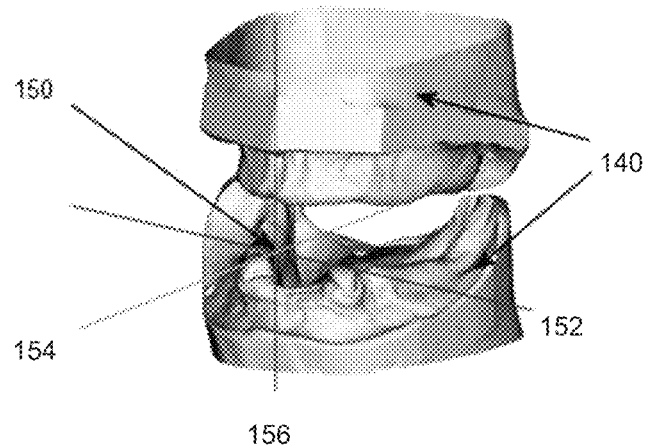
FIG. 5. The prosthetic CAD workspace

When the Model Data is imported into the CAD software, it will have its own coordinate system. That is, any part of the geometry contained in the Model Data can be referenced relative to the fixed physical or datum position 150 in the patient's mouth that will remain static provided the geometry is not transformed in any way. This is the Prosthetic CAD Workspace (FIG. 5). FIG. 5 shows model data 140 of an upper and lower jaw, having a datum of a Cartesian coordinate system 150, where the Cartesian coordinate system as x (152), y (154), and z (156) axes.

Figure 6:
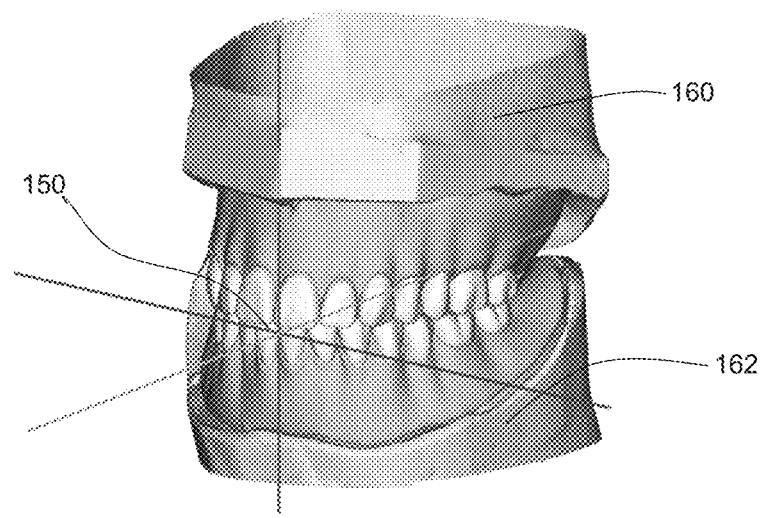
FIG. 6. A prosthetic CAD workspace overlaid with model data.

Furthermore, any geometry added or designed on top of the geometry in the Model Data will also be referenced relative to the same workspace as the Model Data. That is, the Model Data and any additional data (i.e., a representation of teeth or other implants) can be overlaid so that they are together in the same workspace. This is a radiographic template shown as 160 (upper jaw) and 162 (lower jaw) (FIG. 6).

In an embodiment, geometry can then be constructed to form the main body of the Radiographic Template 100 such that the appliance will sit on the geometry within the Model Data. The geometry of the Radiographic Template body is not of any specific design but is constructed so that it can sit with minimal interference onto the patient's jaw, whether that be onto one of, or a combination of, existing teeth, an existing prosthesis/restoration, the gingiva, a screw implanted, or any other body located in the patient's jaw.

Figure 7A:
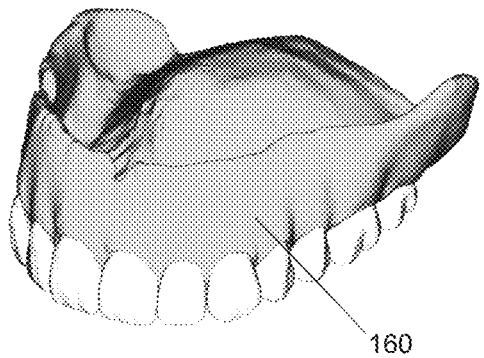
FIG. 7A and FIG. 7B are a perspective and a bottom view, respectively, of a virtual mock-up of a proposed final tooth position.
Figure 7B:
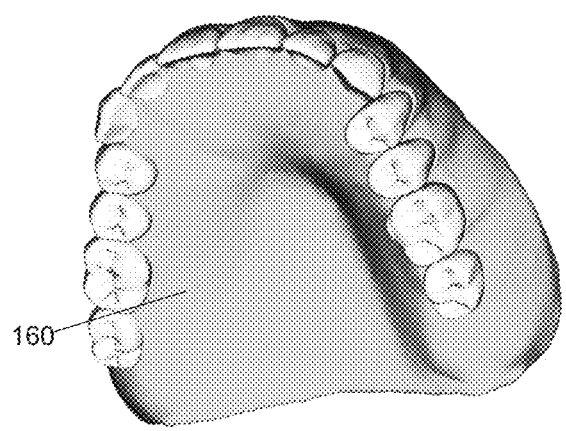

The body of the radiographic template 160 may also contain a virtual mock-up of a proposed Final Tooth Position. (FIGS. 7A and 7B).

Digital data containing the geometry of Radiographic Markers 110 can now be imported into the CAD software. The geometry of the markers is of a known position shape and size. The following description will assume the markers are spheres, although this invention is not limited to that form.

Figure 8:
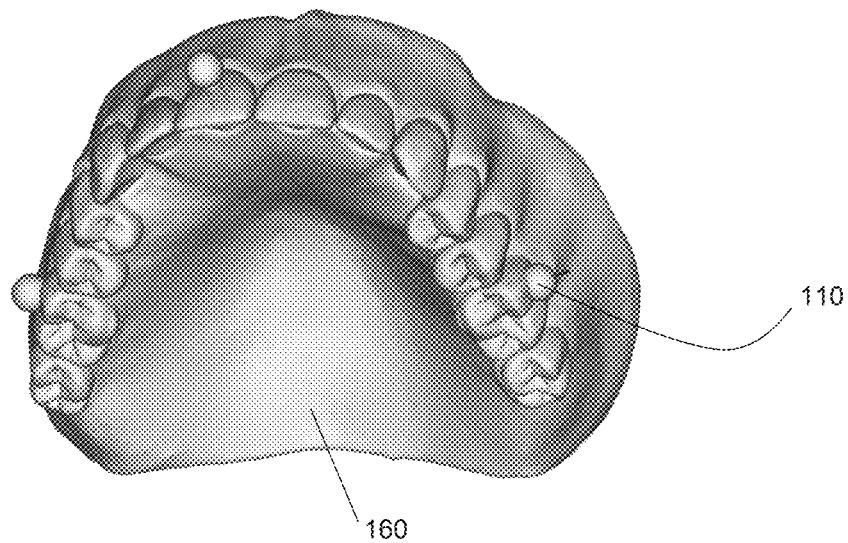
FIG. 8. Positioning of radiographic markers within a radiographic template body.

Three or more spheres 110 (or another radiopaque marker) are overlaid on top of the Radiographic Template design (160). As the spheres are placed in the Radiographic Template, their positions are known. That is, the center of each sphere is recorded as they are placed within the design. (FIG. 8).

The recesses 120 in which the radiopaque markers 110 will sit and locate within the Radiographic Template (160) can be modelled using the CAD software.

Figure 9:
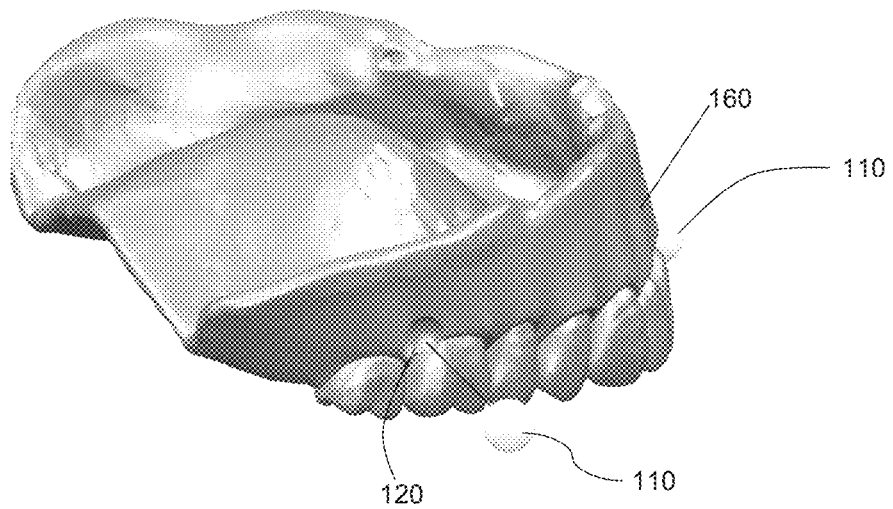
FIG. 9 Radiographic template showing recesses for radiographic markers.

A final Radiographic Template can then be constructed. A physical body of the Radiographic Template may be produced (e.g. using 3D printing, although not limited to that), from a radiolucent material. The Radiographic Markers are produced from a radiopaque material (e.g. zirconia). The Radiographic Markers are seated into the recesses 120 designed in the Radiographic Template and may be held in place using adhesive/cement. (FIG. 9).

Figure 10:
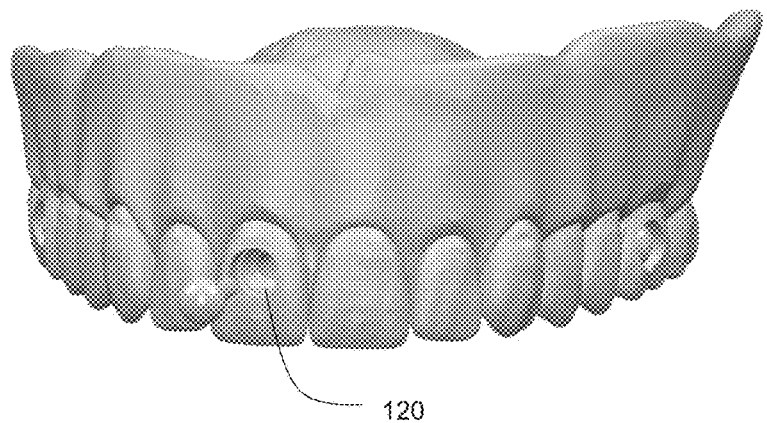
FIG. 10. Another view of a radiographic template showing recesses for radiographic markers.

The Radiographic Markers 110 may further include locating features that will have corresponding and mating geometry cutaway from the Radiographic Template that can help locate and fix the Radiographic Markers in place. It is also possible to position the spheres beneath or embedded within the outer surface of the Radiographic Template, and for the access hole to locate the Radiographic Marker cut away using the CAD software. (FIG. 10).

Alignment of CAD Designed Radiographic Template with CT Data

Figure 11:
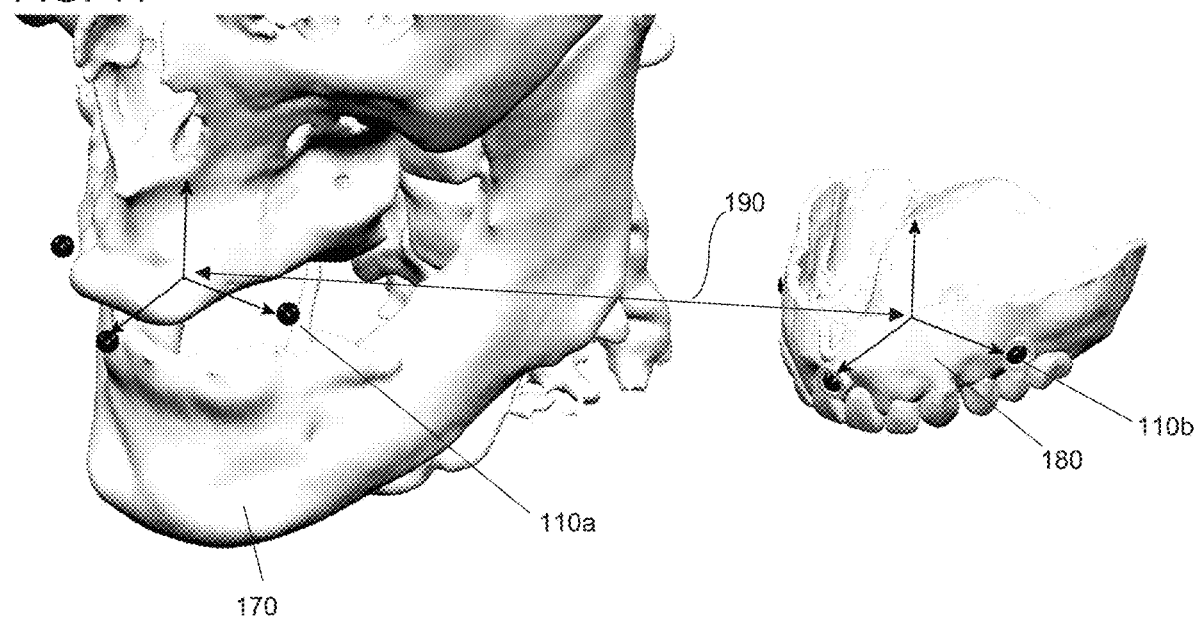
FIG. 11. Prosthetic to CBCT transform, aligning designed radiographic markers with CT image of radiographic markers.

To acquire CBCT data, one (or more) of the radiographic templates as described above is worn by the patient. A CBCT scan is then taken which provides a CBCT workspace (FIG. 11, 170). This is analogous to the acquisition of CT Data 1 (prior art 102) described above. The Marker Segmentation of this CT Scan can be segmented as described above. Now, however, there is no need to scan the radiographic template device (as in the acquisition of CT Data 2 104 in the prior art method) because the location and geometry of the Radiographic Markers 110 is known in advance. The Radiographic marker data is now imported into Implant Planning Software, as opposed to importing the geometry from scans of the radiographic template as in the prior art. It is seen in the CBCT Workspace 170 in FIG. 11 that Radiographic Markers 110a appear to be suspended in space, because this is their actual 3D position in the scan. In this example, a jig as shown in FIG. 4A was used to support the Radiographic Markers.

The Radiographic Markers are of a known geometry and position within the template. This information can be imported into the Implant Planning Software by various means including:

Having the Radiographic Markers exported from the Radiographic Template design software as CAD Data that defines the surface geometry in its respective world position relative to the Prosthetic CAD Workspace. Typical industry wide accepted formats for this CAD Data could include the STL file format (an industry standard CAD file format). The STL file can then be imported into the Implant Planning Software.

Having a means within the Implant Planning Software to directly input definitions of radiographic markers such as by specifying the Cartesian Coordinates of the center of each Radiographic Marker in the Prosthetic CAD Workspace and specifying the geometry type and dimension of the Radiographic Marker (e.g. sphere of a defined diameter).

At this stage we can directly use the method of aligning the Radiographic Markers to the Marker Segmentation as described above. FIG. 11 shows a CBCT workspace 170, a Prosthetic CAD workspace 180, and a Prosthetic to CBCT transform 190.

Correlation Between Prosthetic and CBCT Workspaces

Now, a transformation can be established between the Prosthetic and CBCT Workspaces by applying the methods described above.

The CT Data is stored within a CBCT Workspace. The Radiographic Markers are in the CBCT Workspace are aligned by the Marker Segmentation procedure and are then mapped (or transformed) from the Prosthetic CAD Workspace to the CBCT workspace, i.e., from one coordinate system to another (190). In an embodiment, the markers 110 are transformed from the workspace the markers were designed in, for example the Prosthetic CAD Workspace (180, marker 110b), to the workspace of the CT Data (CBCT Workspace) (170, marker 110a). We now have a direct relationship (Prosthetic to CBCT Transform 190) between the Prosthetic CAD Workspace and the CBCT Workspace and can interchange readily between the two workspaces (FIG. 11). This mapping can be made in either direction, that is, from the CBCT workspace to the Prosthetic CAD Workspace also.

The transformation of coordinates between the Prosthetic CAD Workspace and the CBCT workspace is a mathematical mapping procedure. To allow a three-dimensional coordinate system to be obtained, at least three navigation elements must be provided. The coordinate system may be calculated based on a notional plane extending between the at least three navigation elements, for example. The notional plane may define and extend through perpendicular x- and y-axes, for example. A third axis (e.g., a z-axis) can be determined that is perpendicular to the x- and y-axes. At least one of the navigation elements may be distinguishable from the other navigation elements, e.g. by being structurally different from (e.g., larger or smaller than) one or more others of the navigation elements or by being at an identifiable position of a notional triangle or other shape extending between the navigation elements. This enables a specific location for the third axis (e.g., a z-axis) to be determined, which axis may extend through the distinguishable navigation element in a direction perpendicular to the x- and y-axes. Other known techniques to determine the locations of x-, y- and z-axes based on the positioning of navigation elements (markers) may also be employed.

Figure 11A:
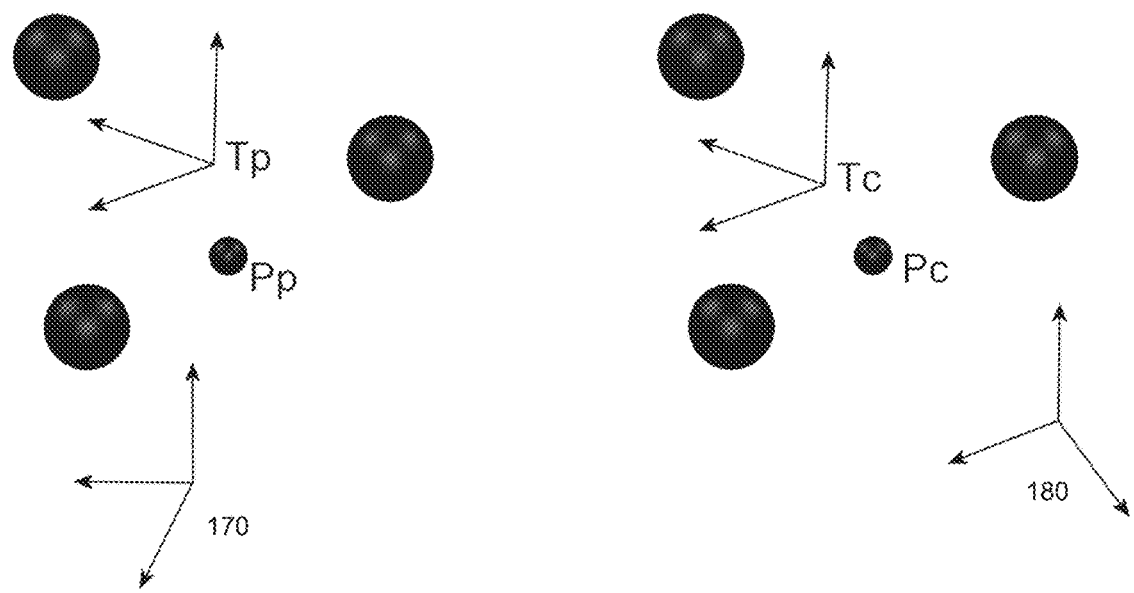
FIG. 11A. Schematic illustration of the prosthetic to CBCT transform.

The transformation can be expressed mathematically with reference to FIG. 11A. If $T_p$ is a transformation matrix representing the coordinate system in Prosthetic CAD Workspace created from the radiographic markers, $T_c$ is a transformation matrix representing the coordinate system in CBCT Workspace created from the radiographic markers, and $T_{pc}$ is the transformation matrix to transform from Prosthetic CAD Workspace to CBCT Workspace, then $$T_{pc} = T_p^{-1} \cdot T_c$$

If $P_p$ is an arbitrary point defined within the Prosthetic CAD Workspace, then $P_c = T_{pc} \cdot P_p$ Consequently, a best-fit between the 3D geometry of the radiographic markers and the segmented markers provides $T_{pc}$.

The navigation elements may comprise objects such as balls or spheres, for example. Additionally or alternatively, the navigation elements may comprise one or more surfaces of an object, e.g., one or more surfaces of a cube.

Thus, in an embodiment, each workspace will be assigned a coordinate system with x, y, and z axes and an origin, and at least three navigational elements are in each workspace corresponding to radiographic markers. The navigational elements define the coordinate system. Once the coordinate system is established in each workspace, any point in either workspace can be mapped to the other workspace. Since the Prosthetic CAD Workspace has predetermined coordinates, an absolute coordinate system that is mapped to actual anatomical landmarks in the patient's mouth can be established.

In an embodiment, the alignment (i.e., mapping) between the two workspaces is accomplished by a best-fit method. This may involve a linear regression mapping between two coordinate systems and an iterative process that is repeated until the coordinates in the two workspaces are closely superimposed. In another embodiment, a linear regression method may be used. In another embodiment, a direct mapping of points by triangulation to the known navigational elements may be used. In this method, a mapped CBCT workspace may be established by triangulation between marker coordinates from marker segmentation of the CBCT scan in the CBCT Workspace, and the 3D geometry of the radiographic markers in the Prosthetic CAD Workspace.

With the inventive method, only a single CBCT scan is necessary. It is not necessary to make a separate impression of the patient's mouth. At the same time, the alignment of the template and patient's mouth is much more straightforward, and the alignment can be much more precise. Also, changes to the workspace during the design process do not require a new data collection process (which is a prior art problem). Also, other prosthetic information can be readily superimposed on the model of the patient's mouth. At the same time, the inventive method allows for a more precise and straightforward alignment of the template with the patient's mouth. Another advantage of the inventive method is that modifications to the workspace during the design process do not require a completely new data collection unlike the processes currently available. Also, other prosthetic information can be readily superimposed on the model of the patient's mouth.

Novel Use of Correlation Between Prosthetic and CBCT Workspaces

As a general method, the Prosthetic to CBCT Transform may be used repeatedly to transform any other data that may be stored in the Prosthetic CAD Workspace to overlay it within the CT Data. This eliminates the need for further alignment of data and allows practitioners to apply the same Prosthetic to CBCT Transform.

Similarly, data can be extracted from the Implant Planning Software, for example data related to the planned implants, or segmentation of the jaw.

The inverse of the Prosthetic to CBCT Transform can also be applied, by transforming the data from the CBCT Workspace to the Prosthetic CAD Workspace. This data can then be imported into the CAD software where it will overlay the data stored within the CAD model.

Importing a Virtual Tooth Setup to Assist Implant Planning

Figure 12:
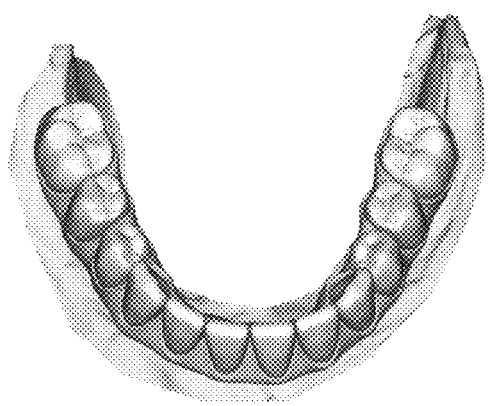
FIG. 12. Final tooth position designed in prosthetic CAD workspace

When the procedure to determine the Prosthetic to CBCT Transform is completed, the CAD software can be used to design the Final Tooth Position for a patient's restoration based on impressions/records taken by the dentist and the subsequent Model Data imported into the CAD software. (FIG. 12).

Figure 13:
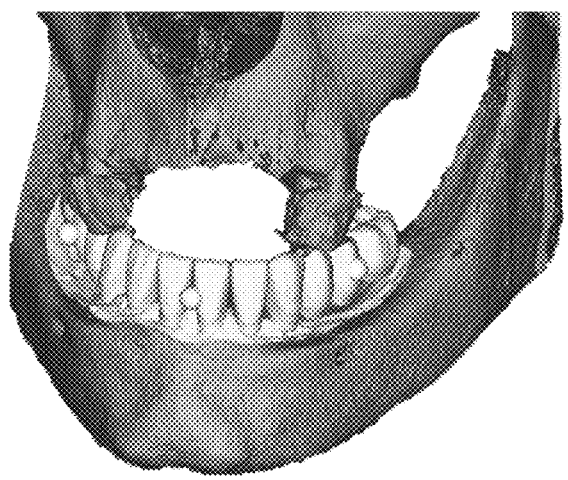
FIG. 13. Final tooth position corrected into the CBCT workspace.

The Prosthetic to CBCT Transform is applied to the 3D geometry of the Final Tooth Position that is subsequently imported into the Implant Planning Software. The precise position of the desired Final Tooth Position can now be used as a further reference for selection and positioning of implants within the CT Data. FIG. 13 shows a final tooth position correlated into the CBCT workspace.

Importing a Final Prosthetic Design to Assist Implant Planning

To assist with the selection and positioning of implants for a dental restoration, overlaying a proposal for the final implant prosthesis design onto the CT Data allows the surgeon to use both the CT Data and bone definition along with proposed or ideal screw access hole positions pre-designed in the prosthesis in a dentally acceptable location. While the final implant position will not necessarily follow exactly the path in the proposed design, it provides another point of reference to greatly assist in providing a predictable outcome.

Figure 14:
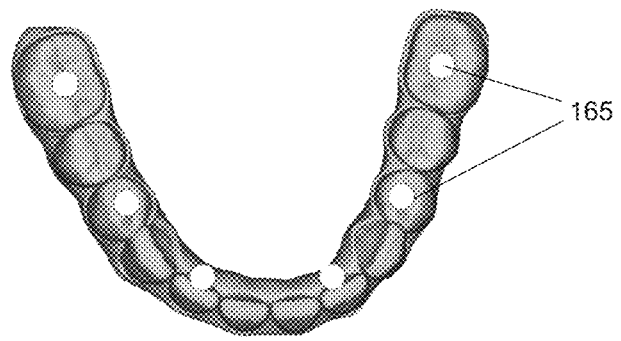
FIG. 14. Substructure of a prosthesis designed in prosthetic CAD workspace.

In this case the Final Tooth Position is first designed in the CAD software. Following this, the substructure of the prosthesis is designed in the CAD software. This substructure is the proposed framework or support for the teeth. Within the substructure the ideal screw hole accesses 165 can be designed in the CAD software and integrated into the substructure design. (FIG. 14).

The Prosthetic to CBCT Transform is applied to design that is subsequently imported into the Implant Planning Software. The design can then be overlaid with the CT Data.

Drawings Legend

| Item No. | Description |
|---|---|
| 100 | Radiographic template |
| 102 | CT Data 1 |
| 104 | CT Data 2 |
| 110 | Radiographic markers |
| 110a | Radiographic marker on CBCT Workspace |
| 110b | Radiographic marker on Prosthetic CAD Workspace |
| 120 | Recesses in radiographic template for radiographic markers |
| 130 | Radiographic jig |
| 140 | Model Data |
| 150 | Datum of Cartesian coordinate system in prosthetic CAD workspace |
| 152 | X axis of Cartesian coordinate system |
| 154 | Y axis of Cartesian coordinate system |
| 156 | Z axis of Cartesian coordinate system |
| 160 | Radiographic template design upper jaw comprising model data with additional data |
| 162 | Radiographic template design lower jaw |
| 165 | screw hole accesses |
| 170 | CBCT Workspace |
| 180 | Prosthetic CAD Workspace |
| 190 | Prosthetic to CBCT transform |

The invention claimed is:

1. A method for the planning of the placement of dental implants in the oral cavity using a radiographic Dental Cone Beam Computer Tomography (CBCT) workspace radiographic template coordinate system and a prosthetic CAD workspace, the method comprising
   a. establishing a radiographic CBCT workspace having a Cartesian coordinate system in the oral cavity of a patient by
      i. placing a radiographic template having at least three radiopaque radiographic markers of predetermined shape, and size, wherein the radiographic template has a predetermined geometry, and wherein the radiographic template is placed in the oral cavity, and mapped to at least one natural or artificial anatomical feature in the oral cavity;
      ii. taking a single CBCT scan of the oral cavity of the patient with the radiographic template in the oral cavity and mapped to at least one natural or artificial anatomical feature in the oral cavity; and
      iii. establishing a radiographic CBCT workspace having a CBCT coordinate system by identifying the radiographic markers with the CBCT scan data and determining the position of the markers;
   b. establishing a prosthetic CAD workspace having a CAD coordinate system from the predetermined location and geometry of the radiographic markers on the radiographic template, and importing the prosthetic CAD workspace into Implant Planning Software; and
   c. mapping the prosthetic CAD workspace to the radiographic CBCT workspace or vice-versa by marker segmentation to establish a direct relationship with a mathematical transformation and the mapped workspace for the planning and placement of dental implants in the oral cavity.

2. The method of claim 1, wherein the radiographic markers are selected from spheres or another 3D geometric shape, whereby each geometric shape is a discrete radiographic marker.

3. The method of claim 1, wherein the radiographic markers are selected from spheres, tetrahedrons, cubes, or icosahedrons or another 3D geometric shape, whereby the geometric data of the radiographic markers are combined to form a coordinate system.

4. The method of claim 1, wherein the radiographic template is a prosthetic appliance placed in the mouth of the patient with three or more radiographic markers at known positions.

5. The method of claim 1, wherein the radiographic template is a jig with three or more radiographic markers with known geometric data, wherein the jig is placed in the mouth of the patient in a location that can be fixed with respect to a natural or artificial anatomical feature in the mouth.

6. A method of establishing a final tooth position of a dental prosthetic design overlaid with the radiographic CBCT workspace and prosthetic CAD workspace of claim 1, wherein the radiographic CBCT workspace and prosthetic CAD workspace are mapped to each other, and CAD software allows a dentist to visualize the patient's mouth in the CAD software, and the dentist can establish final tooth positions of prosthetic implants in the CAD software.

7. The method of claim 6 wherein the radiographic CBCT workspace and prosthetic CAD workspace are mapped to each other by best-fit alignment of marker segmentation of the CBCT scan and the predetermined geometry of the radiographic markers.

8. The method of claim 6 wherein the radiographic CBCT workspace and prosthetic CAD workspace are mapped to each other by triangulation between marker segmentation of the CBCT scan and the predetermined geometry of the radiographic markers.

9. A method of planning dental implant locations and trajectories in the intraoral cavity of patient in need of dental implants, comprising establishing a final tooth position of a dental prosthetic design from the Prosthetic CAD Workspace of claim 1 overlaid with a CBCT scan using a transformed CBCT workspace of claim 1, and selecting appropriate screw locations and trajectories within Implant Planning Software, wherein the screw trajectories intersect with the final tooth positions in a dentally acceptable location.

10. The template of claim 4 wherein the prosthetic appliance placed in the mouth of the patient has four or more radiographic markers at known positions.

* * * * *